US009999349B2

United States Patent
Kato et al.

(10) Patent No.: US 9,999,349 B2
(45) Date of Patent: Jun. 19, 2018

(54) OPHTHALMOLOGIC APPARATUS FOR MEASURING POSITION OF MEASURING PORTION INSIDE EYE

(71) Applicant: TOMEY CORPORATION, Nagoya-shi, Aichi-ken (JP)

(72) Inventors: Chihiro Kato, Nagoya (JP); Tsutomu Ohmori, Nagoya (JP); Yuji Nozawa, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 0 days. days.

(21) Appl. No.: 14/802,913

(22) Filed: Jul. 17, 2015

(65) Prior Publication Data

US 2015/0320309 A1    Nov. 12, 2015

Related U.S. Application Data

(63) Continuation of application No. 13/355,974, filed on Jan. 23, 2012, now Pat. No. 9,119,571.

(30) Foreign Application Priority Data

Feb. 4, 2011   (JP) ................................. 2011-023173

(51) Int. Cl.
*A61B 3/12*      (2006.01)
*A61B 3/117*     (2006.01)
(Continued)

(52) U.S. Cl.
CPC ............ *A61B 3/1173* (2013.01); *A61B 3/102* (2013.01); *A61B 3/1005* (2013.01); *A61B 3/12* (2013.01);
(Continued)

(58) Field of Classification Search
CPC ..... A61B 3/102; A61B 3/1005; A61B 3/1173; A61B 3/12
(Continued)

(56) References Cited

U.S. PATENT DOCUMENTS 4,208,107 A    6/1980  Oharek
5,827,264 A   10/1998  Hohla
(Continued)

FOREIGN PATENT DOCUMENTS

EP    1602320 A1   12/2005
EP    1775545       4/2007
(Continued)

OTHER PUBLICATIONS

Family List and English Translation of Abstract of Japanese Patent Application No. JP-2007275375 published Oct. 25, 2007.
(Continued)

*Primary Examiner* — Zachary Wilkes
(74) *Attorney, Agent, or Firm* — Vierra Magen Marcus LLP

(57) ABSTRACT

An ophthalmologic apparatus comprises a light source 12, an optical measurement system 13 that radiates first light from the light source to inside an eye to be examined and guides first reflected light from the eye, an optical reference system (24, 22) that radiates second light from the light source to a reference surface and guides second reflected light from the reference surface, a photo detector 26 that detects interfering light between the first reflected light from the optical measurement system and the second reflected light from the optical reference system, and a processor that determines a position of a measuring portion of the inside of the eye based on the detected interfering light. The optical measurement system comprises an incident angle changing member 46 that changes an incident angle of the first light (Continued)

radiated to the eye within a predetermined angular range relative to an axis of vision of the eye.

5 Claims, 10 Drawing Sheets

(51) Int. Cl.
*A61B 3/10* (2006.01)
*G01B 9/02* (2006.01)

(52) U.S. Cl.
CPC ..... *G01B 9/02004* (2013.01); *G01B 9/02062* (2013.01); *G01B 9/02064* (2013.01); *G01B 9/02068* (2013.01); *G01B 9/02091* (2013.01)

(58) Field of Classification Search
USPC .................................. 351/206, 221, 208
See application file for complete search history.

(56) References Cited

U.S. PATENT DOCUMENTS

| | | | |
|---|---|---|---|
| 5,847,827 A | 12/1998 | Fercher | |
| 6,806,963 B1 * | 10/2004 | Walti | G01B 11/2441 356/489 |
| 7,370,968 B2 | 5/2008 | Hanebuchi | |
| 7,883,209 B2 | 2/2011 | Murakaimi | |
| 7,884,945 B2 * | 2/2011 | Srinivasan | A61B 3/102 356/479 |
| 7,954,948 B2 | 6/2011 | Nozato et al. | |
| 9,119,571 B2 | 9/2015 | Kato et al. | |
| 2004/0109135 A1 | 6/2004 | Watanabe | |
| 2006/0228011 A1 | 10/2006 | Everett | |
| 2007/0002277 A1 | 1/2007 | Hanebuchi | |
| 2007/0236661 A1 | 10/2007 | Fukuma et al. | |
| 2007/0279592 A1 | 12/2007 | Hanebuchi | |
| 2007/0291230 A1 | 12/2007 | Yamaguchi | |
| 2010/0165289 A1 | 7/2010 | Nozato | |
| 2010/0165291 A1 | 7/2010 | Sugita | |
| 2010/0166293 A1 | 7/2010 | Sugita | |
| 2010/0302508 A1 | 12/2010 | Yamamoto et al. | |
| 2011/0205550 A1 | 8/2011 | Nozato | |

FOREIGN PATENT DOCUMENTS

| | | |
|---|---|---|
| JP | 1-222716 | 8/1995 |
| JP | H09133509 A | 5/1997 |
| JP | 2002336199 A | 11/2002 |
| JP | 2005348755 A | 12/2005 |
| JP | 2007037984 | 2/2007 |
| JP | 2007275375 A | 10/2007 |
| JP | 2007313208 | 12/2007 |
| JP | 2010151713 | 7/2010 |
| WO | WO03/020121 | 3/2003 |
| WO | WO2010/074279 | 7/2010 |
| WO | WO2010125394 | 11/2010 |

OTHER PUBLICATIONS

Machine translation of Japanese Patent Application No. JP-2007275375 published Oct. 25, 2007 prepared by the Japanese Patent Office.
Office Action dated Jul. 15, 2014 in Japanese Patent Application No. 2011-023173, with English translation, 7 pages.
English Translation of Abstract of Japanese Patent Application No. JP-2005-348755.
Machine translation of Japanese Patent Application No. JP-2005-348755 prepared by the Japanese Patent Office.
English Translation of Abstract of Japanese Patent Application No. JP-2002-336199.
Machine translation of Japanese Patent Application No. JP-2002-336199 prepared by the Japanese Patent Office.
"Anterior Segment Optical Coherence Tomography" edited by Roger F. Steinert and David Huang, Slack Incorporated, Chapter 1, pp. 3-4 (2008).
English Translation of Abstract of Japanese Patent Application No. JP-2007-037984.
Machine translation of Japanese Patent Application No. JP-2007-037984 prepared by the Japanese Patent Office.
English Translation of Abstract of Japanese Patent Application No. JP-2007-313208.
Machine translation of Japanese Patent Application No. JP-2007-313208 prepared by the Japanese Patent Office.
European Search Report dated May 21, 2012 European Patent Application No. 12151322.0.
English Translation of Abstract of Japanese Patent Application No. JP2010-151713.
Machine translation of Japanese Patent Application No. JP2010-151713 prepared by the Japanese Patent Office.
Notice of Allowance dated Apr. 20, 2015 in U.S. Appl. No. 13/355,974.
Non-Final Rejection dated Nov. 10, 2014 in U.S. Appl. No. 13/355,974.
Non-Final Rejection dated Oct. 18, 2013 in U.S. Appl. No. 13/355,974.
Amendment dated Mar. 10, 2015 in U.S. Appl. No. 13/355,974.
Amendment dated Aug. 25, 2014 in U.S. Appl. No. 13/355,974.
Amendment dated Mar. 17, 2014 in U.S. Appl. No. 13/355,974.
Final Rejection dated May 23, 2014 in U.S. Appl. No. 13/355,974.
Office Action dated Jul. 31, 2015 in European Patent Application No. 12151322.0, 5 pages.
Office Action dated Jul. 12, 2016 in Japanese Patent Application No. 2015-198802, with English translation.
English abstract of JPH09-133509 published May 20, 1997.
Yun et al.,, "Removing the Depth-Degeneracy in Optical Frequency Domain Imaging with Frequency Shifting", Oct. 4, 2004, vol. 12, No. 20, Optics Express 4823.
Yun et al.,, "High-Speed Optical Frequency-Domain Imaging", Nov. 3, 2003, vol. 11, No. 22, Optics Express 2953.

* cited by examiner

OPHTHALMOLOGIC APPARATUS FOR MEASURING POSITION OF MEASURING PORTION INSIDE EYE

CROSS-REFERENCE TO RELATED APPLICATION

This application is a continuation of U.S. patent application Ser. No. 13/355,974, "OPHTHALMOLOGIC APPARATUS" filed on Jan. 23, 2012, which claims priority to Japanese Patent Application No. 2011-023173 filed on Feb. 4, 2011, both of which are hereby incorporated by reference into the present application.

TECHNICAL FIELD

The present teachings relate to an ophthalmologic apparatus for eye examination.

DESCRIPTION OF RELATED ART

An ophthalmologic apparatus for examining an interior (for example, crystalline lens and retina) of an eye is being developed. The ophthalmologic apparatus of this type is provided with an optical measurement system that radiates light from a light source to inside the eye to be examined and guides the reflected light therefrom, and an optical reference system that radiates light from the light source to a reference surface and guides the reflected light therefrom. A position of a measuring portion (for example, the crystalline lens and retina) inside the eye to be examined is determined from the interfering light between the reflected light guided by the optical measurement system and the reflected light guided by the optical reference system. Conventional examples of ophthalmologic apparatuses of this type are disclosed in Japanese Patent Application Publication Nos. 2007-37984 and 2007-313208.

BRIEF SUMMARY OF INVENTION

In the conventional ophthalmologic apparatus, when the eye to be examined is examined, the focal aim of the light radiated to the eye to be examined is adjusted to match the axis of vision of the eye. However, a normal direction of the crystalline lens typically shifts from the axis of vision of the eye to be examined. For this reason, even when the focal aim of the light radiated to the eye is adjusted so as to match the axis of vision thereof, the light is radiated obliquely to the crystalline lens and light scattering occurs on the surface of the crystalline lens. As a result, in some patients, the light with a sufficient intensity is not reflected from the crystalline lens, and the position of the crystalline lens cannot be determined with good accuracy.

It is an object of the present teachings to provide an ophthalmologic apparatus in which reflected light of sufficient intensity can be observed from the crystalline lens, and the position of the crystalline lens can be determined with good accuracy.

An ophthalmologic apparatus disclosed in the present description includes: a light source, an optical measurement system that radiates light from the light source to inside an eye to be examined and guides reflected light from the eye, an optical reference system that radiates light from the light source to a reference surface and guides reflected light from the reference surface, a photo detector that detects interfering light between the reflected light from the optical measurement system and the reflected light from the optical reference system, and a processor that determines a position of a measuring portion inside the eye based on the interfering light detected by the photo detector. The optical measurement system has an incident angle changing member that changes an incident angle of the light radiated to the eye within a predetermined angular range relative to an axis of vision of the eye.

In such an ophthalmologic apparatus, the incident angle of the light radiated to the eye to be examined can be changed by the incident angle changing member within the predetermined angular range relative to the axis of vision of the eye. Therefore, the incident angle of the light radiated to the crystalline lens can be substantially matched with the normal direction of the crystalline lens, and reflected light of sufficient intensity can be obtained from the crystalline lens. As a result, the position of the crystalline lens can be determined with good accuracy.

DETAILED DESCRIPTION OF INVENTION

In the ophthalmologic apparatus disclosed in the present description, the incident angle changing member may scan the incident angle on the eye to be examined within the predetermined angular range during eye examination, and the photo detector may detect the interfering light of each scan angle. Further, the processor may determine the position of the measuring portion inside the eye to be examined based on interfering light of each scan angle. Where the incident angle on the eye is scanned within the predetermined angular range, the reflected light from the crystalline lens has a sufficient intensity at least at one of the scan angles. Therefore, the processor can determine the position of the crystalline lens with good accuracy.

In the ophthalmologic apparatus disclosed in the present description, the optical measurement system may further include a focal point adjustment mechanism that changes a focal point of the light from the light source in its focal aim direction. With such a configuration, the focal point position of light can be matched at front and rear surfaces of cornea, front and rear surfaces of crystalline lens, and retina. As a result, the intensity of reflected light reflected from these portions is increased and the position of these portions can be determined with good accuracy.

The focal point adjustment mechanism may be configured by a convex lens disposed on a focal aim, a concave lens disposed on the focal aim between the convex lens and the eye, and an actuator that moves the concave lens relative to the convex lens in the focal aim direction.

In the ophthalmologic apparatus disclosed in the present description, the optical measurement system may further include an optical path length changing mechanism that changes an optical path length between the light source and the eye to be examined. With such a configuration, the object optical path length of the optical measurement system can be matched with the reference optical path length of the optical reference system, the intensity of interfering light can be increased, and measurement accuracy can be increased.

In the ophthalmologic apparatus disclosed in the present description, the incident angle changing member may be a mirror disposed on a focal aim of the optical measurement system and this mirror can change the incident angle and an incident position of the light on the eye. In this case, the ophthalmologic apparatus further has a distance adjustment system that adjusts the distance between the mirror and the eye. With such a configuration, the incident position of the light on the crystalline lens can be adjusted by adjusting the distance between the mirror and the eye. As a result, even when lens opacity is present in the crystalline lens due to cataract and the like, light irradiation can be performed by avoiding the lens opacity.

Embodiment

Figure 1:
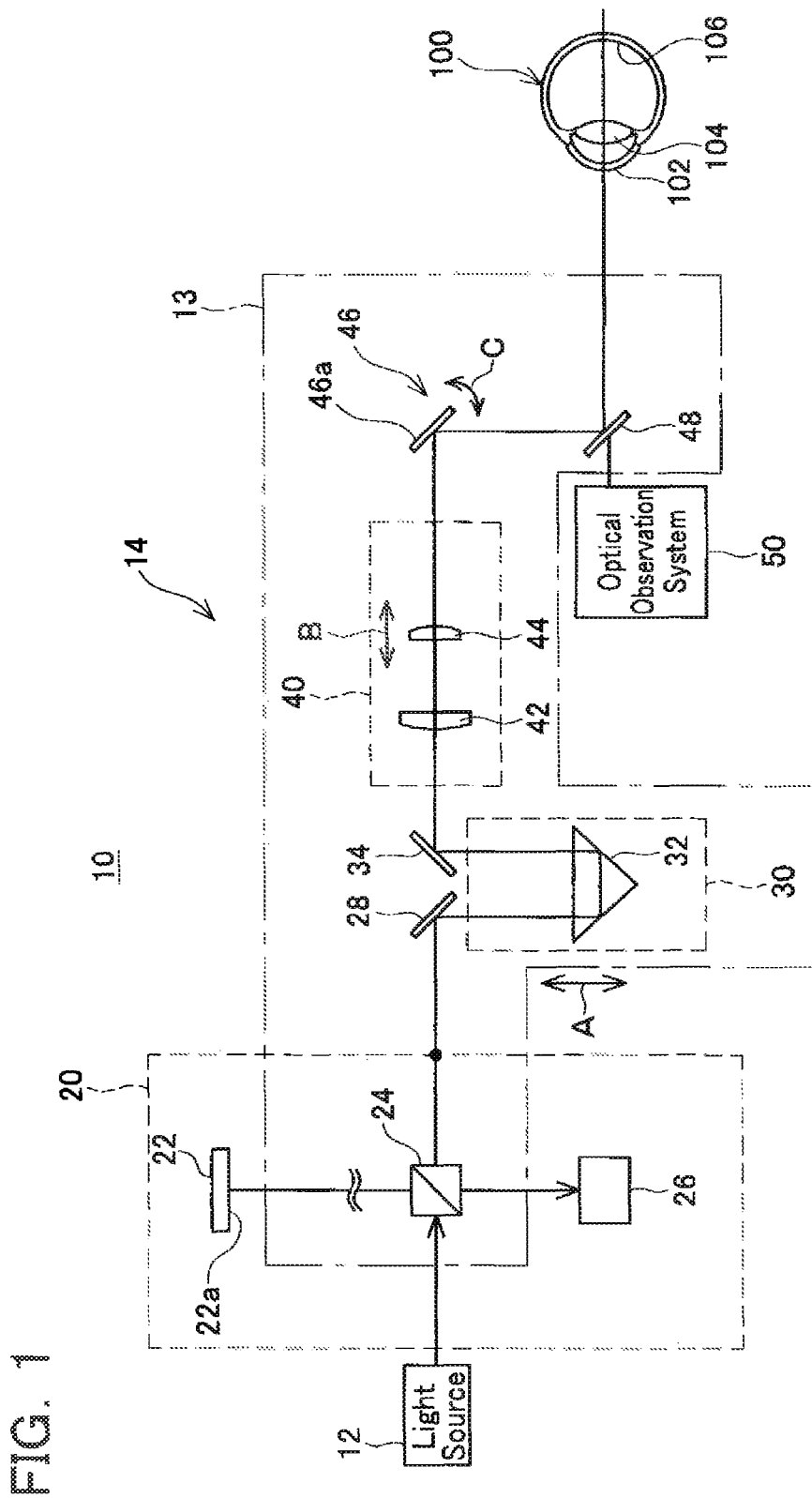
FIG. 1 is a schematic configuration diagram of an optical system of an ophthalmologic apparatus according to the present embodiment.

As shown in FIG. 1, an ophthalmologic apparatus of the present embodiment comprises a measurement unit 10 for examining an eye 100 to be examined. The measurement unit 10 comprises an optical interference system 14 that causes interference of a reflected light that is reflected from the eye 100 and a reference light, an optical observation system 50 that observes an anterior part of the eye 100, and an optical alignment system (not shown in the figure) for aligning the measurement unit 10 with respect to the eye 100 in a predetermined positional relationship. An optical alignment system that has been used in a well-known ophthalmologic apparatus can be used as the aforementioned optical alignment system, and detailed explanation thereof is herein omitted.

The optical interfering system 14 is configured by a light source 12, an optical measurement system 13 that radiates light from the light source 12 to inside the eye 100 and guides reflected light thereof, an optical reference system (22, 24) that radiates light from the light source 12 to a reference surface 22a and guides the reflected light thereof, and a photo detector 26 that detects interfering light between the reflected light guided by the optical measurement system 13 and the reflected light guided by the optical reference system (22, 24).

The light source 12 is of a wavelength sweep type, and a wavelength of the emitted light changes with a predetermined period. Where the wavelength of the light emitted from the light source 12 changes, the reflection position of the reflected light that causes interference with the reference light changes correspondingly to the wavelength of the emitted light. This change in the reflection position takes place in the depth direction of the eye 100. Therefore, the position of each portion (that is, a crystalline lens 104, a retina 106 and the like) inside the eye 100 can be determined by measuring the interfering light, while changing the wavelength of the emitted light.

The optical measurement system 13 is constituted by a beam splitter 24, a mirror 28, a 0 point adjustment mechanism 30, a mirror 34, a focal point adjustment mechanism 40, an incident angle adjustment mechanism 46, and a hot mirror 48. The light emitted from the light source 12 irradiates the eye 100 via the beam splitter 24, mirror 28, 0 point adjustment mechanism 30, mirror 34, focal point adjustment mechanism 40, incident angle adjustment mechanism 46, and hot mirror 48. The reflected light from the eye 100 is guided to the photo detector 26 via the hot mirror 48, incident angle adjustment mechanism 46, focal point adjustment mechanism 40, mirror 34, 0 point adjustment mechanism 30, mirror 28, and beam splitter 24. The 0 point adjustment mechanism 30, focal point adjustment mechanism 40, and incident angle adjustment mechanism 46 will be described in detail hereinbelow.

The optical reference system is constituted by the beam splitter 24 and a reference mirror 22. Part of the light emitted from the light source 12 is reflected by the beam splitter 24, radiated to the reference mirror 22, and reflected by the reference mirror 22. The light reflected by the reference mirror 22 is guided to the photo detector 26 via the beam splitter 24. The reference mirror 22, beam splitter 24, and photo detector 26 are disposed inside an interferometer 20, and the positions thereof are fixed. Therefore, in the ophthalmologic apparatus of the present embodiment, the reference optical path length of the optical reference system is constant and does not change.

The photo detector 26 detects the interfering light between the light guided by the optical reference system and the light guided by the optical measurement system. For example, a photodiode can be used as the photo detector 26.

The optical observation system 50 radiates observation light via the hot mirror 48 on the eye 100 and picks up the reflected light that is reflected from the eye 100 (that is, the reflected light of the radiated observation light). In this case, the hot mirror 48 reflects light from the light source 12 of the optical interference system and transmits light from the light source of the optical observation system 50. As a result, in the ophthalmologic apparatus of the present embodiment, it is possible to perform measurements with the optical interference system and observations of the anterior eye part with the optical observation system 50 at the same time. An optical observation system that has been used in a well-known ophthalmologic apparatus can be used as the optical observation system 50. For this reason, detailed configuration thereof is not explained herein.

Figure 2:
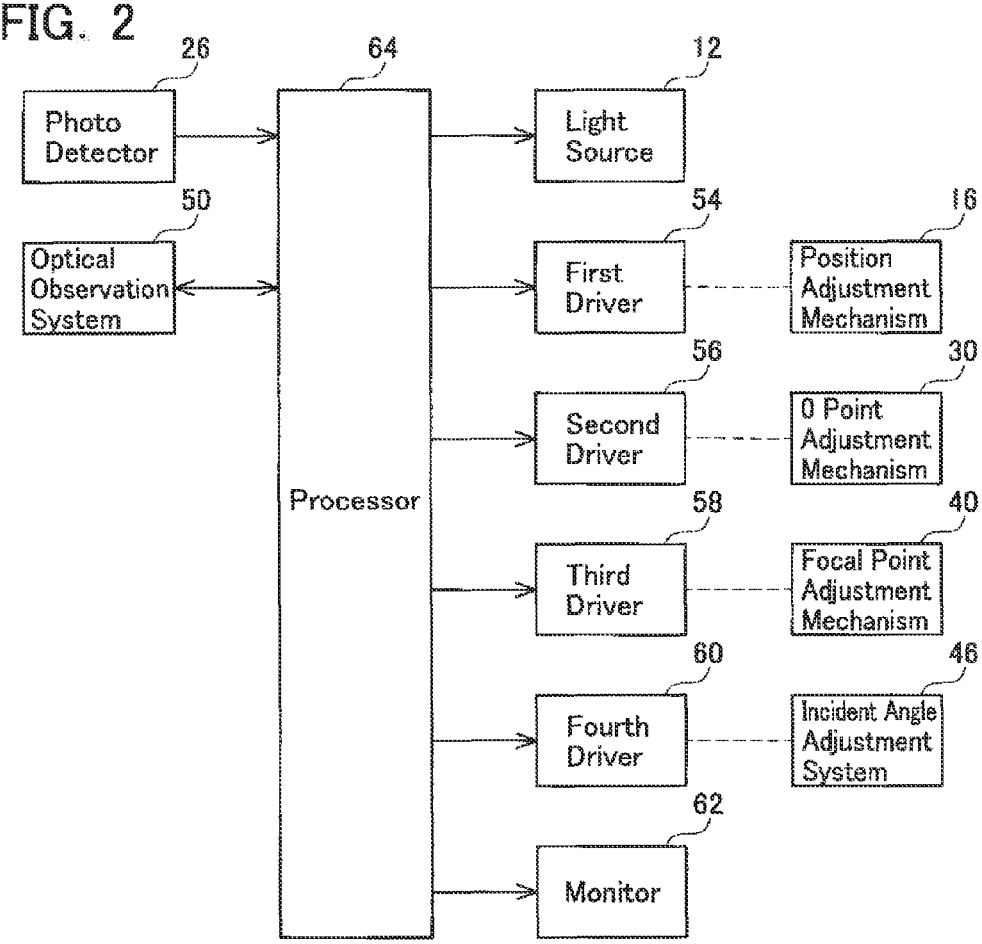
FIG. 2 is a block-diagram of a control system of the ophthalmologic apparatus according to the present embodiment.
Figure 3:
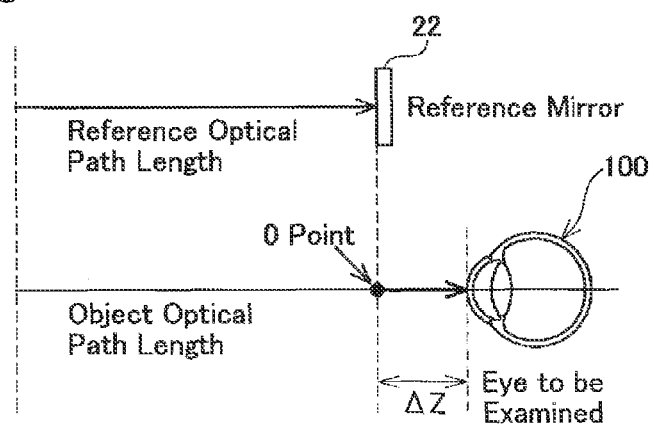
FIG. 3 illustrates functions of a 0 point adjustment mechanism.

The 0 point adjustment mechanism 30, focal point adjustment mechanism 40, and incident angle adjustment mechanism 46 used in the optical measurement system will be explained below. The 0 point adjustment mechanism 30 is provided with a corner cube 32, and a second driver 56 (shown in FIG. 2) that moves the corner cube 32 back and forth with respect to the mirrors 28 and 34. Where the second driver 56 moves the corner cube 32 in the direction of arrow A in FIG. 1, the optical path length (that is, the object optical path length of the optical measurement system) from the light source 12 to the eye 100 changes. As shown in FIG. 3, when there is an optical path difference Δz between the object optical path length from the light source 12 to the detection surface of the eye 100, which is the cornea surface in FIG. 3 (more specifically, light source 12 to detection surface plus detection surface to photo detector 26) and the reference optical path length from the light source 12 to the reference mirror 22 (more specifically, light source 12 to reference mirror 22 plus reference mirror 22 to photo detector 26) is present, the larger is the optical path difference Δz, the lower is the intensity of interfering light between the reflected light that is reflected from the detection surface and the reference light. Conversely, the smaller is the optical path difference Δz, the higher is the intensity of interfering light. Therefore, in the present embodiment, by changing the object optical path length with the 0 point adjustment mechanism 30, it is possible to change the position in which the reference optical path length and the object optical path length match (that is, the 0 point) from the surface of the cornea 102 to the surface of the retina 106.

Figure 4:
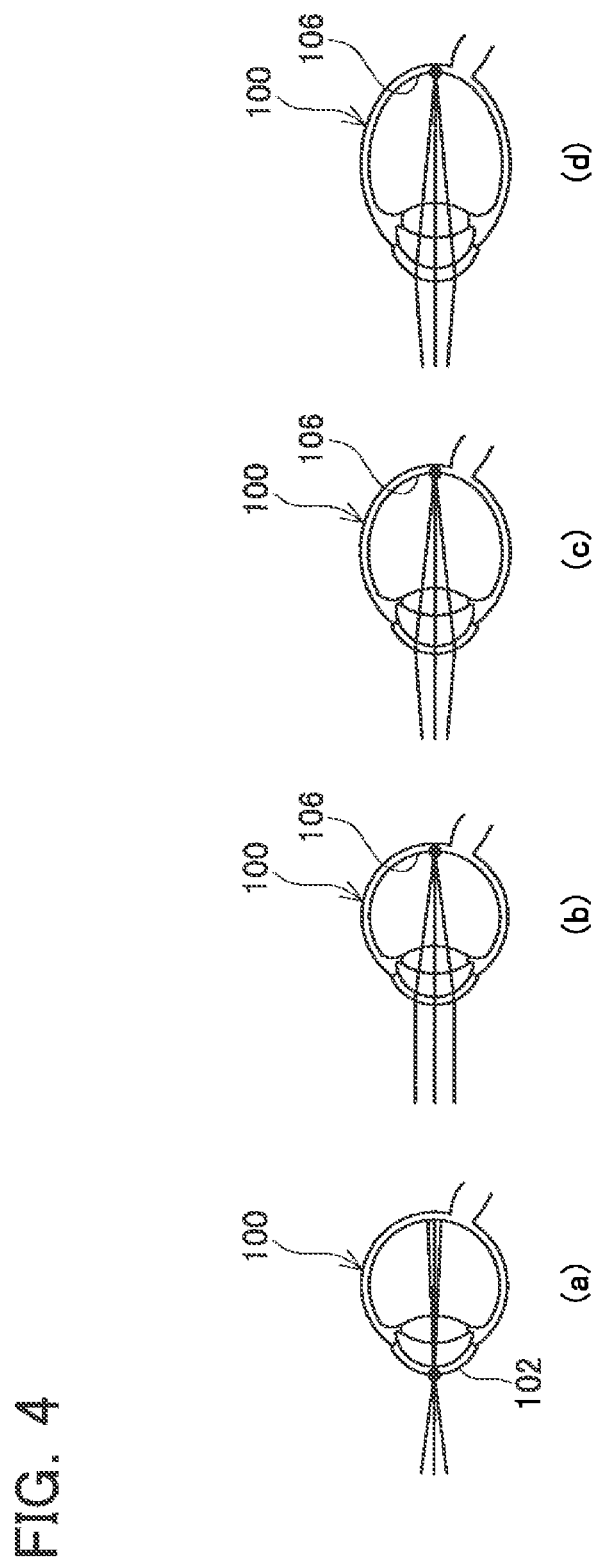
FIGS. 4A to 4D illustrate functions of a focal point adjustment mechanism.

The focal point adjustment mechanism 40 is provided with a convex lens 42 disposed on the light source 12 side, a convex lens 44 disposed on the eye 100 side, and a third driver 58 (shown in FIG. 2) that moves the convex lens 44 back and forth with respect to the convex lens 42 in the focal aim direction. The convex lens 42 and the convex lens 44 are disposed on the focal aim and change a position of a focal point of incident parallel light from the light source 12. Thus, where the third driver 58 drives the convex lens 44 in the direction of arrow B in FIG. 1, the position of the focal point of the light radiated to the eye 100 changes in the depth direction of the eye 100. More specifically, where the convex lens 44 is moved toward the eye 100 from the state in which the distance between the convex lens 42 and the convex lens 44 adjusted so that the light radiated from the convex lens 44 becomes parallel light, the light radiated from the convex lens 44 becomes converged light; and where the convex lens 44 is moved toward the convex lens 42, the light emitted from the convex lens 44 becomes diverging light. Therefore, by adjusting the distance between the convex lens 42 and the convex lens 44, it is possible to change the position of the focal point of the radiated light with respect to the eye 100 of normal vision from the surface of the cornea 102 to the surface of the retina 106, as shown in FIGS. 4A and 4B. Further, the position of the focal point of the radiated light can be also adjusted so as to become the position of the retina 106 with respect to the myopic eye shown in FIGS. 4C and 4D. Thus, by matching the position of the focal point of the light radiated to the eye 100 with the surface of the cornea 102 or the surface of the retina 106 of the eye 100, it is possible to increase the intensity of light reflected from these surfaces and detect the position of these surface with good accuracy.

Figure 5:
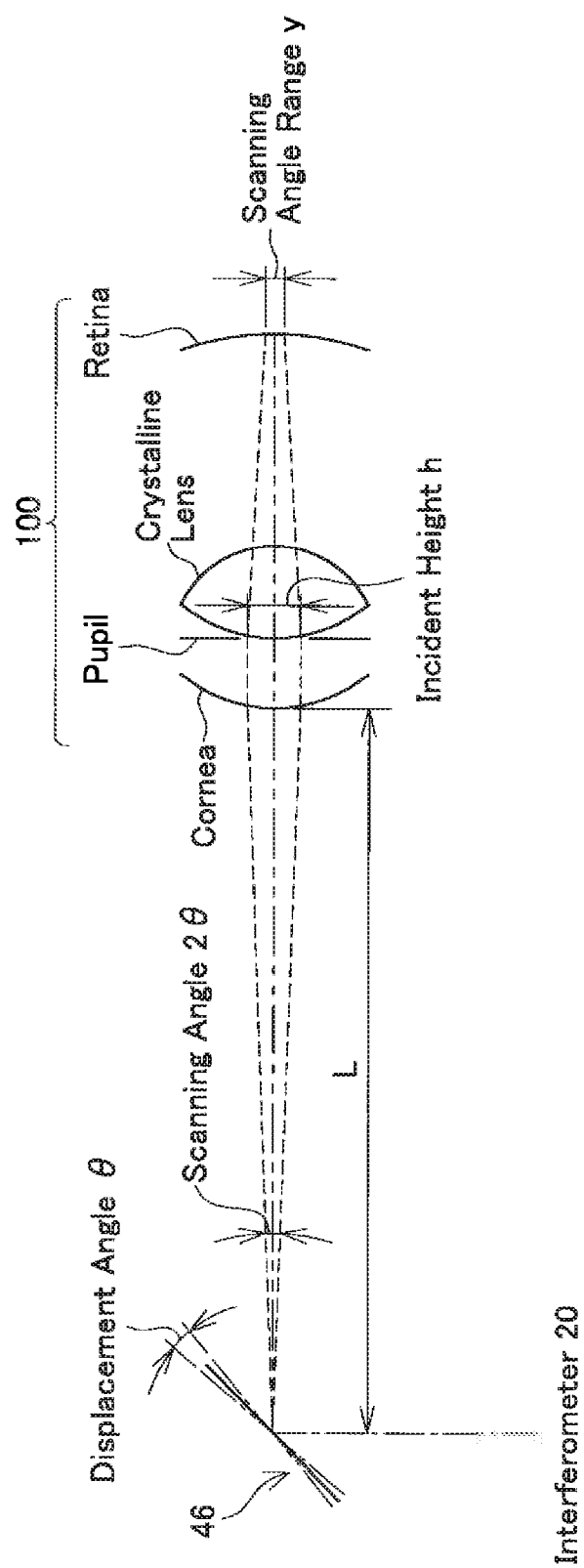
FIG. 5 illustrates functions of a galvano mirror.

The incident angle adjustment mechanism 46 is provided with a galvano mirror 46a and a fourth driver 60 that drives the galvano mirror 46a. The galvano mirror 46a is disposed on the focal aim and can be tilted within a predetermined angular range (for example, ±1°) with respect to the focal aim. Where the fourth driver 60 moves the galvano mirror 46a within the predetermined angular range, the incident position and incident angle of the light radiated to the eye 100 change. Thus, as shown in FIG. 5, the incident position and incident angle of the light on the cornea 102 change according to the displacement angle θ of the galvano mirror 46a. As a result, the incident position and incident angle of the light on the crystalline lens 104 change and the incident position of the light on the retina also changes. Therefore, even if the normal direction of the crystalline lens 104 shifts from the axis of vision, the light can be radiated substantially perpendicularly to the crystalline lens 104. As a result, the intensity of light reflected from the crystalline lens 104 is increased and the position of the crystalline lens 104 can be detected accurately. Further, even when a lens opacity is present in the crystalline lens 104 due to cataract or the like, light irradiation can be performed by avoiding the lens opacity. As a result, the intensity of light transmitted by the crystalline lens 104 can be increased and the position of the retina 106 can be accurately detected.

In the ophthalmologic apparatus of the present embodiment, the tilting direction of the galvano mirror 46a is set so that the incident position of the light radiated to the eye 100 changes in the transverse direction (i.e., direction connecting the left and right eyes). Therefore, the occurrence of the event in which the eye 100 is not irradiated with the light from the light source 12 because of eyelids or eyelashes is prevented.

The ophthalmologic apparatus of the present embodiment is also provided with a position adjustment mechanism 16 (shown in FIG. 2) for adjusting the position of the measurement unit 10 (more specifically, the optical system of the portion of the measurement unit 10 other than the interferometer 20) with respect to the eye 100 and a first driver 54 (shown in FIG. 2) that drives the position adjustment mechanism 16. As clearly follows from FIG. 5, where the position of the measurement unit 10 with respect to the eye 100 is adjusted and the distance L from the eye 100 to the galvano mirror 46a changes, the incident position of the light radiated to the eye 100 also changes accordingly. Therefore, by adjusting the distance L from the eye 100 to the galvano mirror 46a, it is possible to cause the incidence of light on the desired range of the crystalline lens 104. As a result, the lens opacity of the crystalline lens 104 can be adequately avoided. It is also preferred that the distance L from the eye 100 to the galvano mirror 46a be adjusted so that the light radiated to the eye 100 change within the range of the pupil.

The configuration of the control system of the ophthalmologic apparatus of the present embodiment will be described below. As shown in FIG. 2, the ophthalmologic apparatus is controlled by a processor 64. The processor 64 may be constituted by a microcomputer (microprocessor) constituted by CPU, ROM, RAM, and the like. The light source 12, the first to fourth drivers 54 to 60, a monitor 62, and the optical observation system 50 are connected to the processor 64. The processor 64 performs ON/OFF control of the light source 12 and controls the first to fourth drivers 54 to 60, thereby driving the mechanisms 16, 30, 40, and 46. The processor also controls the optical observation system 50 and displays the anterior eye part image picked up by the optical observation system 50 on the monitor 62. The photo detector 26 is also connected to the processor 64, and the interference signal corresponding to the intensity of the interfering light detected by the photo detector 26 is inputted to the processor 64. The processor 64 performs Fourier transform of the interference signal from the photo detector 26 to determine positions of various portions of the eye 100 (e.g., the front and rear surfaces of the cornea 102, front and rear surfaces of the crystalline lens 104, and the surface of the retina 106) and calculate the axial length of the eye 100. The processing performed by the processor 64 to determine the positions of portions of the eye 100 to be examined will be described below in greater detail.

Figure 8:
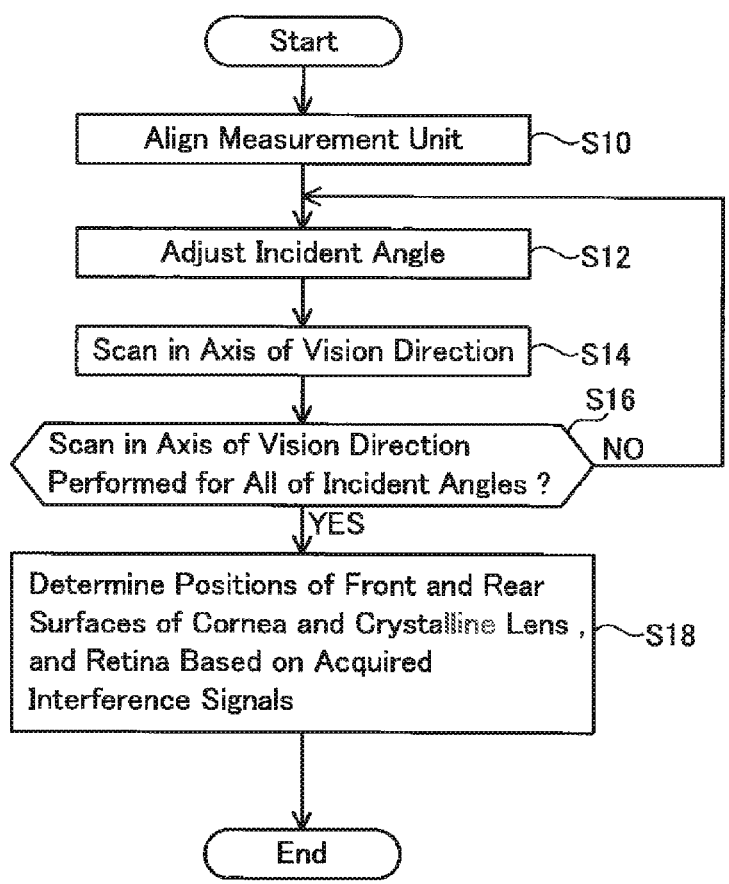
FIG. 8 is a flowchart illustrating an example of processing procedure performed in the ophthalmologic apparatus according to the present embodiment.
Figure 9:
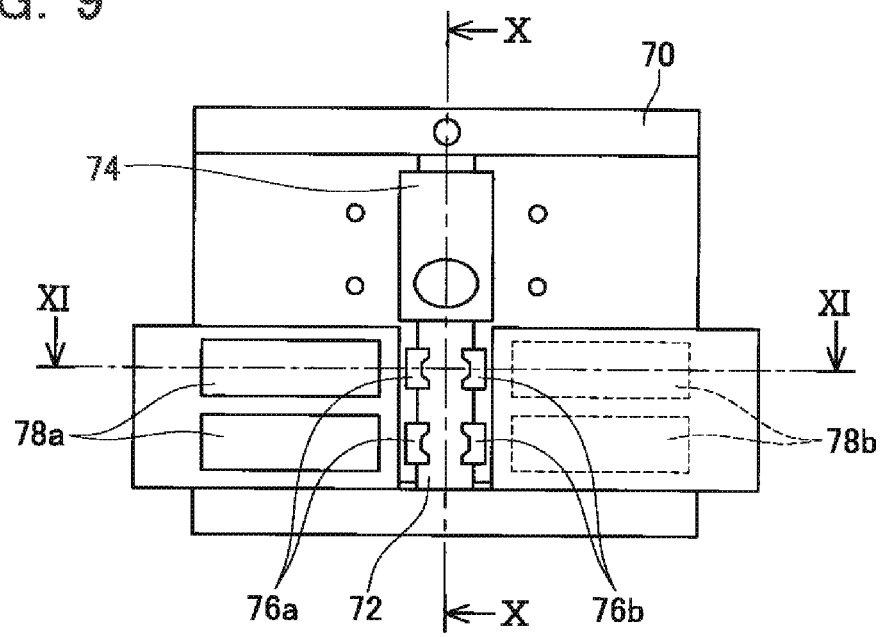
FIG. 9 is a front view illustrating another example of a mechanism changing the incident angle and incident position of the light radiating the eye.
Figure 10:
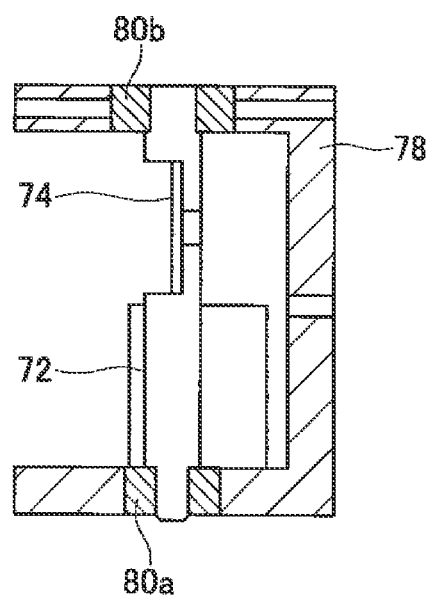
FIG. 10 is a cross-sectional view taken along the X-X line in FIG. 9.

The procedure used to measure the axial length of the eye to be examined by using the ophthalmologic apparatus of the present embodiment will be explained below. As shown in FIG. 8, the operator aligns the measurement unit 10 with respect to the eye 100 by operating an operation member such as a joystick (not shown) (S10). Thus, in response to the operation of the operation member performed by the operator, the processor 64 drives the position adjustment mechanism 16 with the first driver 54. As a result, the position in the xy directions (i.e., longitudinal and lateral directions) and the position in the z direction (i.e., back-forth direction) of the measurement unit 10 with respect to the eye 100 are adjusted. The processor 64 also drives the second and third drivers 56 and 58 to adjust the 0 point adjustment mechanism 30 and the focal point adjustment mechanism 40. As a result, the position of the focal point of the light radiated from the light source 12 to the eye 100 assumes a predetermined position in the eye 100 (for example, the front surface of the cornea 102), and the position of 0 point where the object optical path length and reference optical path length match assumes a predetermined position in the eye 100 (for example, the front surface of the cornea 102).

Figure 6:
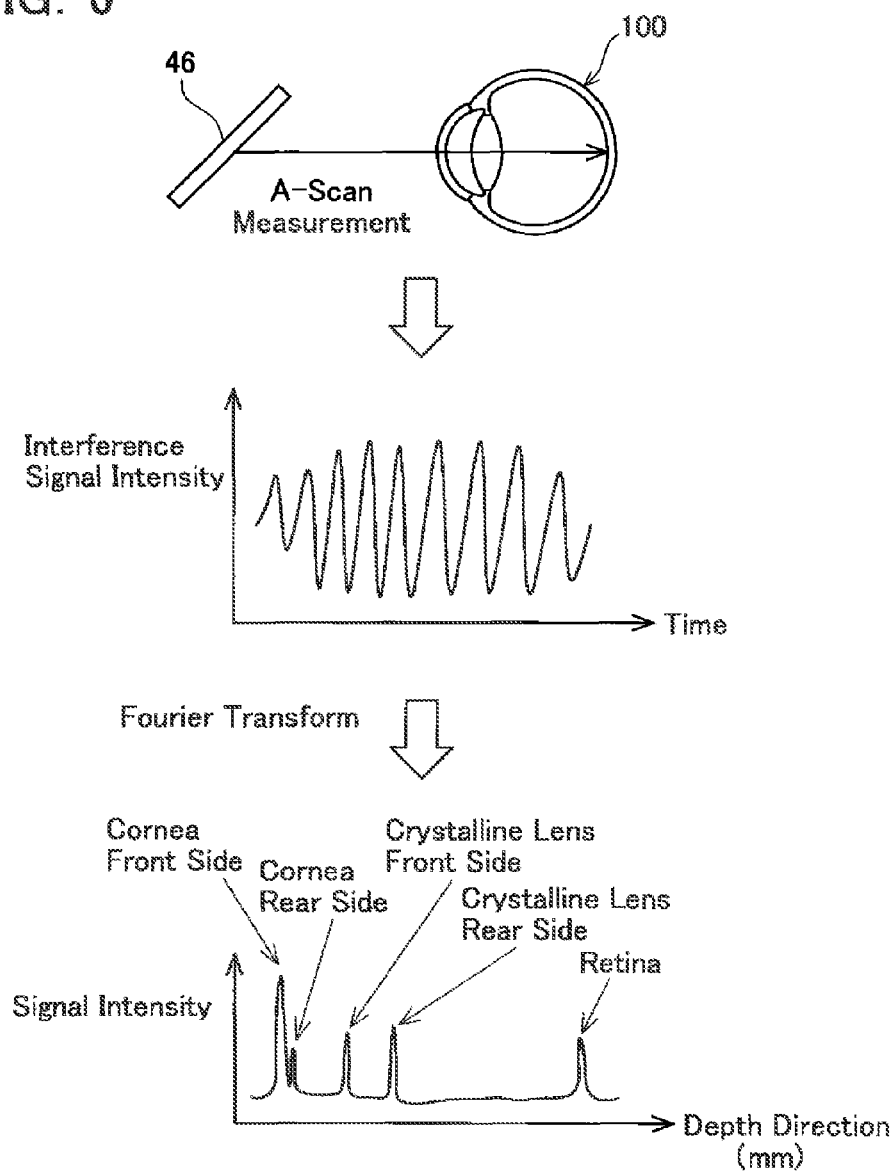
FIG. 6 illustrates the procedure of processing an interference signal waveform obtained when an optical path length of an optical measurement system is scanned within a predetermined optical path length range.

The processor 64 then drives the fourth driver 60 and adjusts the galvano mirror 46a to a scan angle within a scan angle range (S12). As a result, the light from the light source 12 falls on the eye 100 at the incident position and incident angle corresponding to the adjusted scan angle.

Where the adjustment of the galvano mirror 46a is completed, the processor 64 takes in the signal detected by the photo detector 26, while changing the frequency of light radiated from the light source 12 (S14). As has already been explained, where the frequency of light radiated from the light source 12 changes, the position where the measurement light interferes with the reference light and an interfering wave is generated changes in the depth direction of the eye 100. Therefore, the interference signal outputted from the photo detector 26 becomes a signal with intensity changing with time, as shown in FIG. 6, and this signal includes signals created by the interfering wave between the reference light and reflected light that has been reflected from various parts (e.g., front surface and rear surface of the cornea 102, front surface and rear surface of the crystalline lens 104, and surface of the retina 106) of the eye 100. Accordingly, the processor 64 performs Fourier transform of the signal inputted from the photo detector 26, thereby separating the interference signal component created by the reflected light reflected from various parts (e.g., front surface and rear surface of the cornea 102, front surface and rear surface of the crystalline lens 104, and surface of the retina 106) of the eye 100. The processor 64 thus can determine the positions of various portions of the eye 100 to be examined. In the present description, the process of changing the position where the interference occurs in the depth direction of the eye 100 by changing the frequency of the light radiated from the light source 12 is called A-scan.

Figure 7:
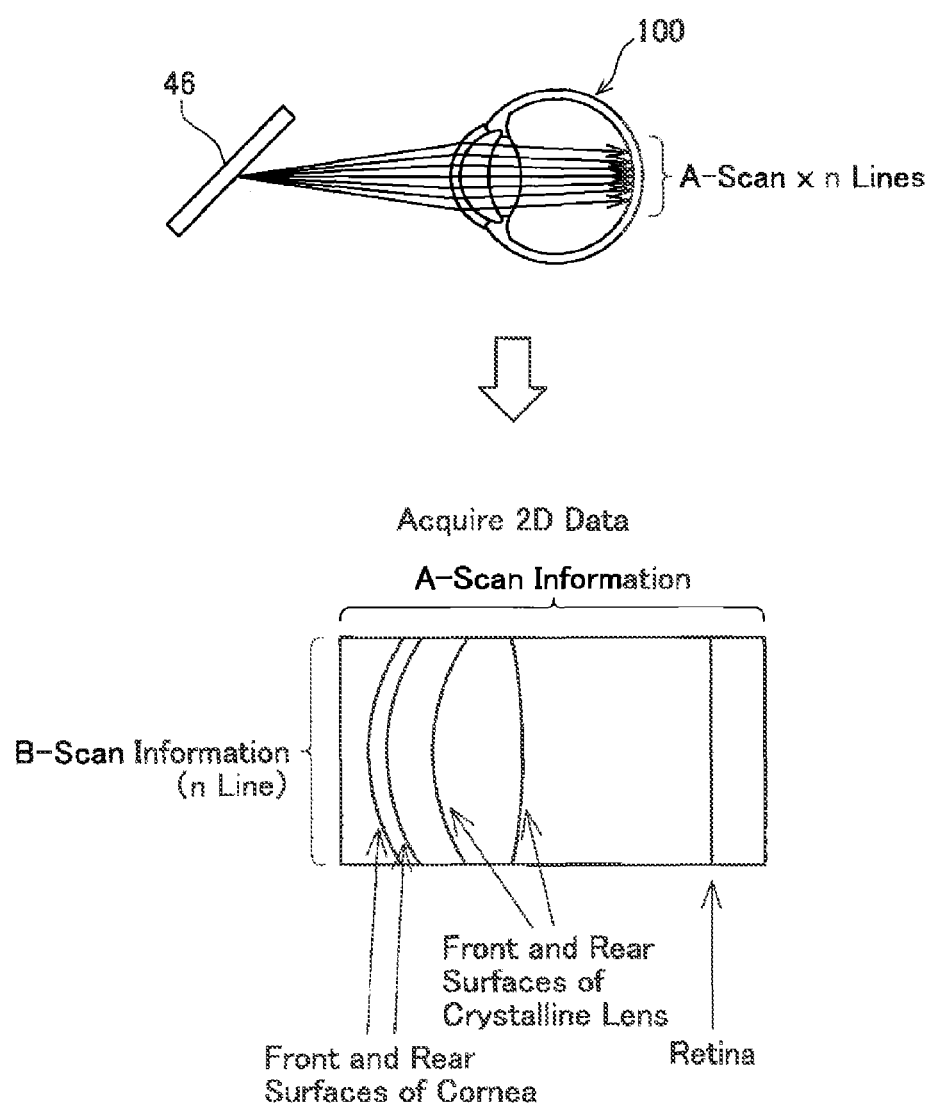
FIG. 7 illustrates a procedure of scanning an incident angle of light on an eye to be examined within the predetermined angular range and determining positions of each portion of the eye from information (i.e., information obtained by the procedure shown in FIG. 6) obtained with respect to each scan angle.

The processor 64 then determines whether or not the measurement of the above-described step S14 has been performed with respect to all of the scan angles (that is, all of the incident positions and incident angles) (S16). Where the measurement of step S14 has not been performed with respect to all of the scan angles (NO in step S16), the processing is returned to step S12 and repeated from step S12. As a result, the interference signal obtained by A-scan is acquired for each scan angle of the galvano mirror 46a. In the present description, the process of changing the incident position and incident angle of light from the light source 12 by changing the scan angle (oscillation angle θ) of the galvano mirror 46a is called B-scan.

Where the measurement of step S14 has been performed with respect to all of the scan angles (YES in step S16), the processor 64 determines the position of each portion of the eye 100 (that is, the positions of the front surface and rear surface of the cornea 102, front surface and rear surface of the crystalline lens 104, and surface of the retina 106) (S18). More specifically, where the processing of step S14 is performed with respect to each scan angle, information on interference signals (i.e., A-scan information) is acquired with respect to each scan angle. Therefore, as shown in FIG. 7, two-dimensional information is obtained in which interference signal information (i.e., A-scan information) is arranged in a row correspondingly to the number (n) of scan angles. Therefore, by calculating the average value of position information of the portions of the eye 100 that is included in each type of interference signal information (that is, the front surface and rear surface of the cornea 102, front surface and rear surface of the crystalline lens 104, and surface of the retina 106), the processor 64 determines the position of each portion of the eye 100. Where the position of each portion of the eye 100 can be determined, the processor 64 calculates the axial length of the eye 100. The position of each portion of the eye 100 and the axial length of the eye calculated in the above-described manner are displayed on the monitor 62.

As follows from the explanation above, in the ophthalmologic apparatus according to the present embodiment, the incident position and incident angle of light radiated to the eye 100 to be examined are scanned within predetermined ranges by scanning the oscillation angle θ of the galvano mirror 46a. Then, interference signal waveforms in the axial direction of the eye to be examined are acquired with respect to each scan angle (oscillation angle θ) of the galvano mirror 46a and the positions of portions of the eye 100 to be examined (that is, the positions of the front surface and rear surface of the cornea 102, front surface and rear surface of the crystalline lens 104, and surface of the retina 106) are determined from these interference signal waveforms. Therefore, since the A-scan information is acquired by radiating light to the crystalline lens 104 at various incidence angles, the A-scan information for which the intensity of reflected light from the crystalline lens 104 is sufficient is included in the obtained measurement results. Therefore, the position of the crystalline lens 104 can be determined with good accuracy. Further, since the incident position of light on the crystalline lens 104 changes, even when an lens opacity is present in the crystalline lens 104 due to cataract or the like, A-scan information that is measured by avoiding the lens opacity is included in the obtained measurement results. Therefore, even when a lens opacity is present in the crystalline lens 104 due to cataract or the like, the position of each portion of the eye can be determined with good accuracy.

Specific embodiment of the present teachings is described above, but this merely illustrates some representative possibilities for utilizing the present teachings and does not restrict the claims thereof. The subject matter set forth in the claims includes variations and modifications of the specific examples set forth above.

For example, in the above-described embodiment, the incident angle and incident position of light radiated to the eye 100 is adjusted (changed) by the galvano mirror 46a, but it is also possible to change only the incident angle of light radiated to the eye 100. In such a configuration, the light can be also radiated to the crystalline lens 104 at various angles. Therefore, the position of the crystalline lens 104 can be determined with good accuracy.

Figure 11:
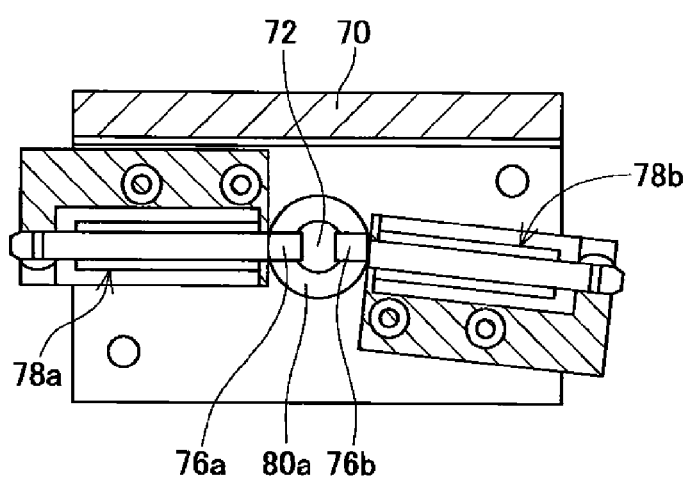
FIG. 11 is a cross-sectional view taken along the XI-XI line in FIG. 9 and showing a state in which a shaft is rotated counterclockwise to the maximum limit.
Figure 12:
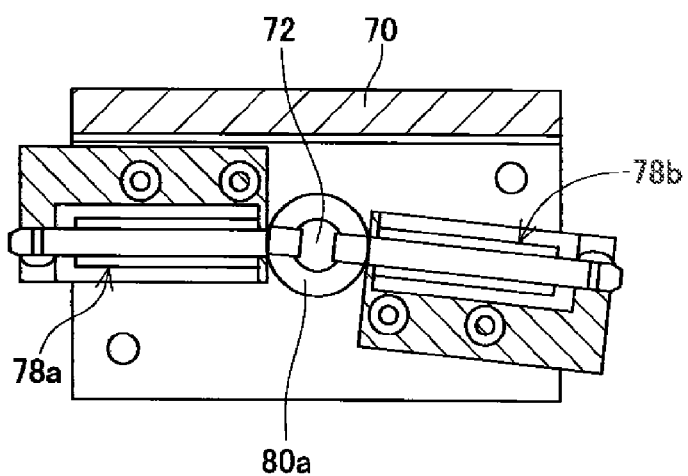
FIG. 12 is a cross-sectional view taken along the XI-XI line in FIG. 9 and showing a state in which the shaft is rotated clockwise to the maximum limit.

Further, in the above-described embodiment, the galvano mirror 46a is used to change the incident angle and incident position of light radiated to the eye 100, but the incident angle and incident position of light radiated to the eye to be examined may alternatively be changed by using other configuration. For example, the incident angle and incident position of the light radiated to the eye may be changed by using a mirror and an electromagnet driving the mirror. In the example shown in FIGS. 9 to 12, a housing 70 rotatably supports both ends of a shaft 72 by bearings 80a, 80b. A mirror 74 and a plurality of magnets 76a, 76b are mounted on the shaft 72. The magnet 76a is disposed on the left shaft of the shaft 70, and the magnet 76b is disposed on the right side of the shaft 70. Electromagnets 78a, 78b are disposed at positions opposite the magnets 76a, 76b. In such a configuration, where the ratio of the current flowing to the electromagnet 78a disposed on the left side of the shaft 72 and the current flowing electromagnet 78b disposed on the right side of the shaft 72 is changed, magnetic forces acting from the left and right electromagnets 78a, 78b upon the magnets 76a, 76b are changed. As a result, the shaft 72 rotates with respect to the housing 70 and a transition is made from the state shown in FIG. 11 (a state in which the magnet 76a disposed on the left side of the shaft 72 is attracted to the electromagnet 78a disposed of the left side of the shaft 72) to the state shown in FIG. 12 (a state in which the magnet 76b disposed on the right side of the shaft 72 is attracted to the electromagnet 78b disposed on the right side of the shaft 72). Therefore, by controlling the ratio of currents flowing to the left and right electromagnets 78a, 78b, it is possible to control the rotation angle of the shaft 72. Where the rotation angle of the shaft 72 changes, the incident angle of light to the mirror 74 mounted on the shaft 72 also changes. Therefore, with the above-described configuration, by controlling the ratio of currents flowing to the left and right electromagnets 78a, 78b, it is possible to change the incident angle and incident position of the light radiated to the eye to be examined.

Figure 13:
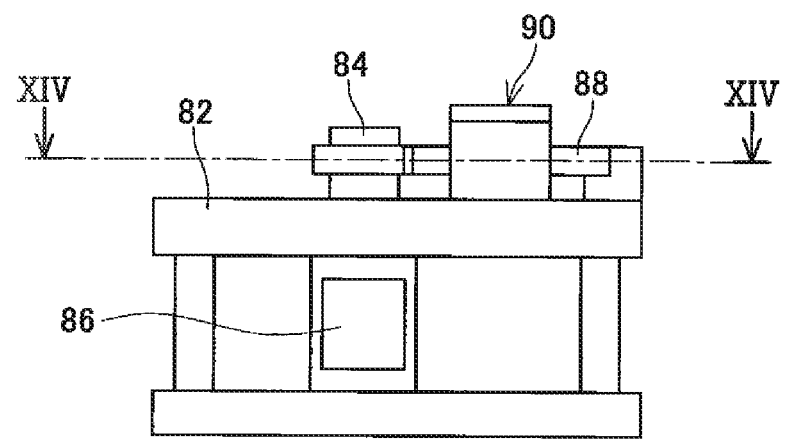
FIG. 13 is a front view illustrating another example of the mechanism changing the incident angle and incident position of the light radiating the eye.
Figure 14:
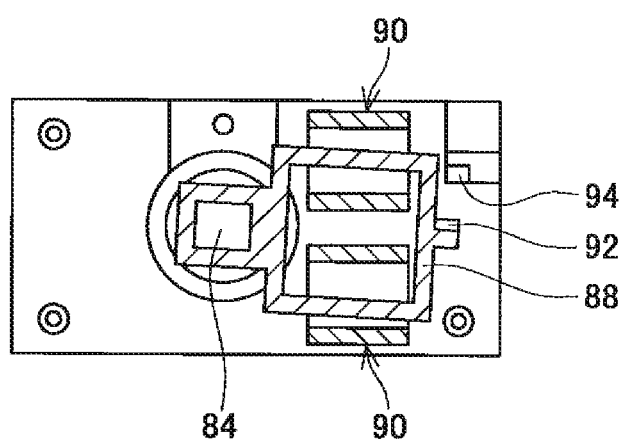
FIG. 14 is a cross-sectional view taken along the XIV-XIV line in FIG. 13 and showing a state in which the shaft is rotated clockwise to the maximum limit.
Figure 15:
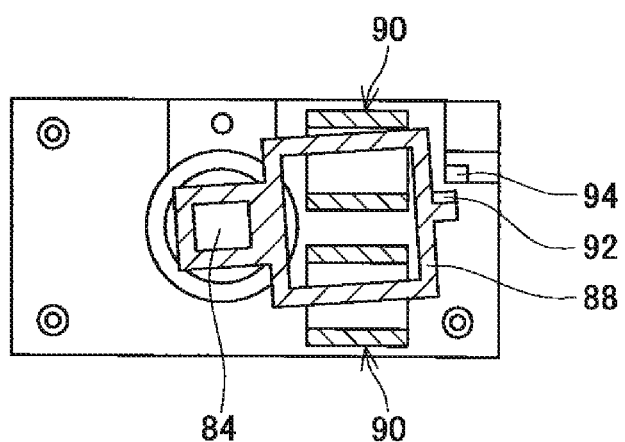
FIG. 15 is a cross-sectional view taken along the XIV-XIV line in FIG. 13 and showing a state in which the shaft is rotated counterclockwise to the maximum limit.

The configuration in which the mirror is driven by the electromagnets is not limited to the configuration shown in FIGS. 9 to 12, and various other configurations can be used. For example, in the example shown in FIGS. 13 to 15, a shaft 84 is supported rotatably with respect to a housing 82. A mirror 86 is mounted on the shaft 84. A coil holder 88 is mounted on the upper end of the shaft 84. A coil (not shown in the figure) is wound on the coil holder 88. Magnet parts 90 are disposed on the two sides of the coil holder 88 that face each other. The magnet parts 90 are disposed on the upper surface of the housing 82. The magnet part 90 is provided with a pair of magnets sandwiching the coil holder 88 in the up-down direction. A magnetic field directed from top to bottom of the coil holder 88 is formed by the pair of magnets. In addition, a magnet 92 is mounted on the outer circumferential surface of the coil holder 88, and a magnet 94 is mounted on the housing 82. The magnet 92 and the magnet 94 are disposed so as to face each other, and a repulsive force acts between the magnet 92 and the magnet 94. In such a configuration, in a state in which no current flows in the coil wound on the coil holder 88, a clockwise momentum acts upon the coil holder 88 due to the repulsive force of the magnet 92 and the magnet 94, and the coil holder 88 is biased to the state shown in FIG. 14. By contrast, where a current flows through the coil wound on the coil holder 88, a counterclockwise Lorenz force acts upon the coil holder 88. As a result, the coil holder 88 rotates counterclockwise to a position in which the Lorenz force is balanced by the repulsive force of the magnet 92 and the magnet 94 (for example, a state shown in FIG. 15). Therefore, by controlling the amount of current flowing through the coil wound on the coil holder 88, it is possible to control the Lorenz force acting upon the coil holder 88 and control the rotation angle of the coil holder 88. Where the coil holder 88 rotates, the shaft 84 also rotates integrally with the coil holder 88, and the incident angle of light to the mirror 86 mounted on the shaft 84 changes. As a result, it is possible to change the incident angle and incident position of light radiated to the eye. Therefore, the above-described configuration also makes it possible to change the incident angle and incident position of light radiated to the eye.

Further, in the above-described embodiment, the position of the focal point of light radiated to the eye 100 and the 0 point position are adjusted to a predetermined position of the eye 100 and the frequency of light emitted from the light source 12 is changed at this position, but a variety of methods can be used to determine the positions of various portions of the eye 100. For example, the position of the focal point of the light radiated to the eye 100 to be examined and the 0 point position are matched with the position of the front surface of the cornea 102 of the eye 100, the frequency of light emitted from the light source 12 is changed at this position, and interference signals relating only to the positions of the front surface and rear surface of the cornea 102 are acquired. Then, the position of the focal point of the light radiated to the eye 100 and the 0 point position are matched with the position of the front surface of the crystalline lens 104 of the eye 100, the frequency of light emitted from the light source 12 is changed at this position, and interference signals relating only to the positions of the front surface and rear surface of the crystalline lens 104 are acquired. Finally, the position of the focal point of the light radiated to the eye 100 and the 0 point position are matched with the position of the front surface of the retina 106 of the eye 100, and the interference signal relating only to the position of the front surface of the retina 106 is acquired. Where the focal point position and 0 point position are thus matched with various portions of the eye and a plurality of measurements is conducted, the intensity of interfering light created by reflected light from these portions is intensified and the position of each portion can be determined with good accuracy.

Further, in the above-described embodiment, the positions of portions of the eye 100 to be examined are determined by simply averaging the two-dimensional information obtained by A-scan and B-scan, but such a method is not limiting. For example, this method may be changed when determining the retina 106 and other portions (i.e., cornea 102 and crystalline lens 104). That is, the interference signal obtained with the reflected light from the retina 106 shows little dependence on B-scan. This is because the dependence of the incident angle is small due to diffusion reflection of light incident on the retina 106. Accordingly when the position of the retina 106 is determined, the position of the retina 106 can be determined by adding up and averaging the position information obtained for all of the scan angles. By adding up the position information obtained for all of the scan angles, it is possible to remove noise and increase the S/N ratio. By contrast, the interference signal produced by the reflected light from the cornea 102 and the crystalline lens 104 shows strong dependence on B-scan. This is because the incident light undergoes mirror reflection on the cornea 102 and the crystalline lens 104. Accordingly, when the position of the cornea 102 or the crystalline lens 104 is determined, the position of the cornea 102 or the crystalline lens 104 is determined by adding up and averaging only the position information obtained with respect to an angular range with increased intensity of interference signal. As a result, the effect of B-scan is reduced and the positions of the cornea 102 and the crystalline lens 104 can be determined with good accuracy.

Further, in the above-described embodiment, the position of the measurement unit 10 is adjusted by the operator operating the operation member, but the ophthalmologic apparatus may also have a mechanism for automatic adjustment of the position of the measurement unit 10 with respect to the eye 100. Moreover, in the above-described embodiment, an example is described in which an interferometer of a Fourier domain system is used, but an interferometer of a time domain system may be also used.

Further, the configurations of the optical system shown in the above-described embodiment are merely examples and various modifications thereof can be used. For example, in the above-described embodiment, the focal point adjustment mechanism 40 is constituted by two convex lenses 42, 44, but the focal point adjustment mechanism can be also configured of a convex lens disposed on the light source side and a concave lens disposed on the eye side of the mechanism. In this case, similarly to the above-described embodiment, where the concave lens is moved toward the eye from a state in which the distance between the convex lens and the concave lens has been adjusted so that the light radiated to the eye becomes parallel light after the concave lens, the light radiated on the eye becomes converging light after the concave lens, and where the concave lens is moved toward the convex lens, the light radiated to the eye becomes diffused light after the concave lens.

What is claimed is:

1. An ophthalmologic apparatus comprising:
   a light source;
   an optical measurement system configured to radiate first light from the light source to inside an eye to be examined and guides first reflected light from the eye;
   an optical reference system configured to radiate second light from the light source to a reference surface and guides second reflected light from the reference surface;
   a photo detector configured to perform a measurement operation to detect interfering light between the first reflected light from the optical measurement system and the second reflected light from the optical reference system; and
   a processor that determines a first position of a first measuring portion inside the eye based on the detected interfering light and a second position of a second measuring portion inside the eye based on the detected interfering light, the processor further determining an axial length from the first position to the second position,
   wherein the optical measurement system comprises a focal point adjustment mechanism configured to change a focal point of the first light in its focal aim direction and a match point adjustment mechanism configured to change an optical path length between the light source and the eye in order to change a match point in which the optical path length between the light source and the eye matches an optical path length between the light source and the reference surface,
   the processor is further configured to conduct the measurement operation by changing both the match point and the focal point of the first light in its optical axis direction during the measurement operation such that the focal point of the first light is matched with each of a front or rear surface of a cornea of the eye, a front or rear surface of a crystalline lens of the eye, and a surface of a retina of the eye during the measurement operation,
   the processor is further configured to determine the first position of the first measuring portion during the measurement operation based on the first detected interfering light obtained when a wavelength of emitted light from the light source is swept in a first state where the focal point and the match point are matched with the first position,
   the processor is further configured to determine the second position of the second measuring portion during the measurement operation based on the second detected interfering light obtained when a wavelength of the emitted light from the light source is swept in a second state where the focal point and the match point are matched with the second position,
   the light source is a wavelength sweep type and configured to enable a measurement of an axial length of the eye, which is a distance from a cornea of the eye to a retina of the eye, in a state where the focal point and the match point are matched with a front surface of the cornea of the eye,
   the first position of the first measuring portion is one of: a front or rear surface of the cornea of the eye; a front or rear surface of a crystalline lens of the eye; and a surface of the retina of the eye, and
   the second position of the second measuring portion is one of: the front or rear surface of the cornea of the eye; the front or rear surface of the crystalline lens of the eye; and the surface of the retina of the eye, and different from the first position.

2. The ophthalmologic apparatus as in claim 1, wherein the first position of the first measuring portion is the front or rear surface of the cornea of the eye,
   the second position of the second measuring portion is the surface of the retina of the eye, and
   the processor determines the axial length of the eye.

3. The ophthalmologic apparatus as in claim 1, wherein the optical measurement system comprises an incident angle changing member configured to change an incident angle of the first light radiated to the eye within a predetermined angular range relative to an axis of vision of the eye,
   the incident angle changing member is configured to scan the incident angle within the predetermined angular range during a measurement,
   the photo detector is configured to detect interfering light of each scan angle and outputs an interference signal of each scan angle to the processor,
   the interference signal of each scan angle includes a first signal component and a second signal component, the first signal component being created by the first reflected light and reflected light from the first position of the first measuring portion, and the second signal component being created by the second reflected light and reflected light from the second position of the second measuring portion, the first position of the first measuring portion is one of a front or rear surface of a cornea of the eye, and a front or rear surface of a crystalline lens of the eye, and the processor is configured to determine the first position of the first measuring portion based on only the first signal component of the interference signal with respect to an angular range with increased intensity of the interference signal which is higher than a predetermined intensity.

4. The ophthalmologic apparatus as in claim 3, wherein the processor is further configured to determine the second position of the second measuring portion based on the second signal component of the interference signal of all of the scan angles within the predetermined angular range.

5. An ophthalmologic apparatus comprising:

a light source;

an optical measurement system configured to radiate first light from the light source to inside an eye to be examined and guides first reflected light from the eye;

an optical reference system configured to radiate second light from the light source to a reference surface and guides second reflected light from the reference surface;

a photo detector configured to detect interfering light between the first reflected light from the optical measurement system and the second reflected light from the optical reference system; and a processor that determines a first position of a first measuring portion inside the eye based on the detected interfering light and a second position of a second measuring portion inside the eye based on the detected interfering light, the processor further determining an axial length from the first position to the second position, wherein the optical measurement system comprises a focal point adjustment mechanism configured to change a focal point of the first light in its focal aim direction and a match point adjustment mechanism configured to change an optical path length between the light source and the eye in order to change a match point in which the optical path length between the light source and the eye matches an optical path length between the light source and the reference surface, the processor is further configured to conduct the measurement by changing both the match point and the focal point of the first light in its optical axis direction during the measurement such that the focal point of the first light is matched with each of a front or rear surface of a cornea of the eye, a front or rear surface of a crystalline lens of the eye, and a surface of a retina of the eye during the measurement, the processor is further configured to determine the first position of the first measuring portion based on the first detected interfering light obtained when a wavelength of emitted light from the light source is swept in a first state where the focal point and the match point are matched with the first position, the processor is further configured to determine the second position of the second measuring portion based on the second detected interfering light obtained when a wavelength of the emitted light from the light source is swept in a second state where the focal point and the match point are matched with the second position, the light source is a wavelength sweep type and configured to enable a measurement of an axial length of the eye, which is a distance from a cornea of the eye to a retina of the eye, in a state where the focal point and the match point are matched with a front surface of the cornea of the eye, the first position of the first measuring portion is one of: a front or rear surface of the cornea of the eye; a front or rear surface of a crystalline lens of the eye; and a surface of the retina of the eye, and the second position of the second measuring portion is one of: the front or rear surface of the cornea of the eye; the front or rear surface of the crystalline lens of the eye; and the surface of the retina of the eye, and different from the first position wherein the processor is configured to determine the first position of the first measuring portion based on only a first signal component of an interference signal with respect to an angular range with increased intensity of the interference signal which is higher than a predetermined intensity.

* * * * *